United States Patent
Li (10) Patent No.: US 10,144,771 B2
(45) Date of Patent: Dec. 4, 2018

(54) LUNG CANCER DIAGNOSIS MARKER, ANTIBODY AND APPLICATION THEREOF

(71) Applicant: Chong Li, Beijing (CN)

(72) Inventor: Chong Li, Beijing (CN)

( * ) Notice: Subject to any disclaimer, the term of this patent is extended or adjusted under 35 U.S.C. 154(b) by 0 days.

(21) Appl. No.: 15/710,794

(22) Filed: Sep. 20, 2017

(65) Prior Publication Data

US 2018/0094042 A1   Apr. 5, 2018

Related U.S. Application Data

(63) Continuation of application No. PCT/CN2016/076593, filed on Mar. 17, 2016.

(30) Foreign Application Priority Data

Mar. 27, 2015   (CN) .......................... 2015 1 0142768

(51) Int. Cl.

| | | |
|---|---|---|
| C07K 16/00 | (2006.01) |
| C07K 14/705 | (2006.01) |
| G01N 33/574 | (2006.01) |
| G01N 33/577 | (2006.01) |
| A61K 47/68 | (2017.01) |
| A61P 35/00 | (2006.01) |
| C07K 16/30 | (2006.01) |
| A61K 49/18 | (2006.01) |
| C07K 16/28 | (2006.01) |
| C07K 16/44 | (2006.01) |
| C07K 14/47 | (2006.01) |

(52) U.S. Cl.
CPC ...... *C07K 14/7055* (2013.01); *A61K 47/6857* (2017.08); *A61K 49/1875* (2013.01); *A61P 35/00* (2018.01); *C07K 14/4748* (2013.01); *C07K 16/2842* (2013.01); *C07K 16/3023* (2013.01); *C07K 16/44* (2013.01); *G01N 33/574* (2013.01); *G01N 33/577* (2013.01); *G01N 33/57423* (2013.01); *C07K 2317/14* (2013.01); *G01N 2800/7028* (2013.01)

(58) Field of Classification Search
None
See application file for complete search history.

(56) References Cited

U.S. PATENT DOCUMENTS

2009/0291853 A1   11/2009   Kim et al.

FOREIGN PATENT DOCUMENTS

| CN | 104761634 A | 7/2015 |
| WO | 2009009114 A2 | 1/2009 |

OTHER PUBLICATIONS

Dionet et al (Anticancer Res, 1983, 3(4): Abstract).*
Cited in the International Search Report and Written Opinion issued by the Chinese Patent Office dated Jun. 22, 2016, in connection with International Application No. PCT/CN2016/076593.

* cited by examiner

*Primary Examiner* — Sean E Aeder
(74) *Attorney, Agent, or Firm* — Corridor Law Group, P.C.

(57) ABSTRACT

A human lung cancer marker N3G4, and use of the same as human lung cancer marker is disclosed. Hybridoma cells which produce anti-N3G4 monoclonal antibodies, and the secreted monoclonal antibody LC128, and use of LC128 for the preparation of a diagnostic agent for lung cancer are also disclosed. Kits for in vitro diagnosis comprising the monoclonal antibody LC128 and methods for detecting tumor markers in lung tissue by using the monoclonal antibody LC128 are also disclosed.

14 Claims, 4 Drawing Sheets
Specification includes a Sequence Listing.

MNLQPIFWIGLISSVCCVFAQTDENRCLKANAKSCGECIQAGPNCGWCTNSTFLQEGMPTSARC
DDLEALKKKGCPPDDIENPRGSKDIKKNKNVTNRSKGTAEKLKPEDITQIQPQQLVLRLRSGEPQ
TFTLKFKRAEDYPIDLYYLMDLSYSMKDDLENVKSLGTDLMNEMRRITSDFRIGFGSFVEKTVM
PYISTTPAKLRNPCTSEQNCTSPFSYKNVLSLTNKGEVFNELVGKQRISGNLDSPEGGFDAIMQVA
VCGSLIGWRNVTRLLVFSTDAGFHFAGDGKLGGIVLPNDGQCHLENNMYTMSHYYDYPSIAHLV
QKLSENNIQTIFAVTEEFQPVYKELKNLIPKSAVGTLSANSSNVIQLIIDAYNSLSSEVILENGKLSE
GVTISYKSYCKNGVNGTGENGRKCSNISIGDEVQFEISITSNKCPKKDSDSFKIRPLGFTEEVEVIL
QYICECECQSEGIPESPKCHEGNGTFECGACRCNEGRVGRHCECSTDEVNSEDMDAYCRKENSSE
ICSNNGECVCGQCVCRKRDNTNEIYSGKFCECDNFNCDRSNGLICGGNGVCKCRVCECNPNYTG
SACDCSLDTSTCEASNGQICNGRGICECGVCKCTDPKFQGQTCEMCQTCLGVCAEHKECVQCRA
FNKGEKKDTCTQECSYFNITKVESRDKLPQPVQPDPVSHCKEKDVDDCWFYFTYSVNGNNEVM
VHVVENPECPTGPDIIPIVAGVVAGIVLIGLALLLIWKLLMIIHDRREFAKFEKEKMNAKWDTGEN
PIYKSAVTTVVNPKYEGK

FIG. 5

LUNG CANCER DIAGNOSIS MARKER, ANTIBODY AND APPLICATION THEREOF

CROSS-REFERENCE TO RELATED APPLICATIONS

This application is a continuation of International Application No. PCT/CN2016/076593 having an international filing date of Mar. 17, 2016 entitled "Lung Cancer Diagnosis Marker, Antibody and Application Thereof". The '593 international application claimed priority benefits, in turn, from Chinese Patent Application No. 201510142768.7 filed on Mar. 27, 2015. The '593 international application is hereby incorporated by reference herein in its entirety.

FIELD OF THE INVENTION

The present invention relates to the field of tumor immunology. Specifically, it relates to a novel lung cancer tumor marker N3G4, and an anti-N3G4 monoclonal antibody LC128. It has been shown on cellular and histology levels that LC128 can specifically recognize human lung cancer cells and human lung cancer tissue. The present disclosure also relates to a method for detecting human lung cancer by using immunomagnetic beads. The target antigen in the detection method is the novel human lung cancer marker N3G4 of the present disclosure, and the antibody used for the detection is the monoclonal antibody LC128 against human lung cancer marker N3G4.

Lung cancer is one of the most common malignant tumors in China. The incidence and mortality of lung cancer in China is increasing year by year. According to the data issued by National Center for Cancer Registries in 2014, there were 605,900 new cases of lung cancer in China in 2010, accounting for 19.59% of new cases of cancers, and topping the list of cancers. Most patients had proceeded to an advanced stage before diagnosis, and thus fail to be treated at an earlier stage. Two common types of lung cancer are small cell lung cancer (SCLC) (16.8%) and non-small cell lung cancer (NSCLC) (80.4%). Non-small cell lung cancer mainly includes squamous cell carcinoma, pulmonary adenocarcinoma and large cell lung cancer, among which pulmonary adenocarcinoma is the most common lung cancer (30%-65%). The pathogeny of lung cancer is not yet known.

Current medical studies have focused on the diagnosis and treatment of lung cancer at earlier stage. Statistically, non-small cell lung cancer patients at an earlier stage have a 5-year survival of up to 80%, while the total 5-year survival for non-small cell lung cancer is only 15% (Mulshine J L, Sullivan D. Clinical Practice. Lung cancer screening [J]. N Engl J Med, 2005, 352 (26): 271422720). Thus, it is important to diagnose and treat lung cancer at an earlier stage.

Current methods for the diagnosis of lung cancer include sputum cytology, image testing, endoscopy, and biopsy. The sensitivity of sputum cytology is low. Imaging test methods commonly used for lung cancer include X-ray, CT, MRI (magnetic resonance imaging), ultrasound, nuclide imaging, PET-CT (positron emission tomography/computed tomography), and the like. Imaging test methods are also relatively unsensitive, and usually only a lesion more than 1 cm in size is visible. In endoscopy, a tumor is visible only when it resides in airway accessible to an endoscope. Low-dose chest CT has limited sensitivity, although it is the most recognized diagnosis method. Like X-ray testing, CT involves ionizing radiation which itself can lead to cancer. The diagnostic rate for earlier-stage patients not displaying typical symptoms is only 15% (ZHU, Jinfang et al., Research development of blood tumor marker in the lung cancer early diagnosis [J]. Medical Review, 2010, 16(7): 1015-1018). Traditional methods for screening lung cancer lacking in their usefulness in high-risk populations due to their limited specificity and sensitivity, onerous nature, and high cost. These traditional methods fail to significantly decrease the mortality of lung cancer. There is a need for an alternative or supplemental method for screening lung cancer to increase diagnostic rate for early lung cancer, and reduce the number of surgical operations to lower the risk of complications.

In recent years, tumor markers have provided a direction for the diagnosis, classification, prognosis, and treatment of tumors due to their high specificity and sensitivity. It has been shown that integrin $\beta 1$ is involved in the invasion and metastasis of lung cancer cells (GONG Xue, CHEN Lizhu, et al., Progress of Study on Integrin and Invasion and Metastasis of Tumors [J]. 2007, 23(15):2288-2289). Integrin is a heterodimer consisting of a subunit and $\beta$ subunit. Integrin is functionally involved in the adhesion of cells to substrates and cells to cells, signaling of cells, regulation of proliferation and apoptosis of cells, adhesion, invasion, and metastasis of tumor cells, and angiogenesis. $\beta 1$ subunit (CD29) and $\alpha 3$ subunit (CD49c) of integrin form a dimer. Integrin $\alpha 3\beta 1$ mediates the direct adhesion of cells to components of extracellular matrix. Furthermore, the abnormal modification of integrin $\alpha 3\beta 1$ results in a change in the malignancy of tumor cells. Therefore, it is important to develop a new modification form of integrin for the diagnosis and treatment of lung cancer.

SUMMARY OF INVENTION

A hybridoma cell strain can be obtained by immunizing a mouse with a fresh human lung cancer tissue. An antibody, LC128, is obtained by screening using ELISA, which belongs to IgG1 subgroup and can bind to human lung cancer tissue with a high specificity. It has been demonstrated by immunohistochemistry and flow cytometry that the antibody LC128 shows a strong positive reaction with human lung cancer tissues and lung cancer cell lines, A549, Calu-3, NCI-H1975, NCI-H460, SK-LU-1, NCI-H157 while is not cross-reactive with normal human lung tissues and other non-lung cancer cells.

It has been identified by immunoprecipitation in combination with mass spectrum and carbohydrate chip test that the antigen recognized by the antibody LC128 is an abnormally glycosylated $\beta 1$ subunit of integrin located on a cell membrane and having an epitope of Neu5Ac$\alpha$2-6GlcNAc$\beta$1-3Gal$\beta$1-3GlcNAc$\beta$1-3Gal$\beta$1 which is a new lung cancer marker.

The antibody LC128 can be coupled with magnetic nanoparticles to form anti-lung cancer immunomagnetic beads (LC128-MB). After being mixed with hydrothorax from a patient, the beads capture and enrich exfoliated lung cancer cells. Then, diagnosis can be performed under a microscope after Wright-Giemsa pathological staining. The kit is useful for early screening, prognosis monitoring, and pathologically assisted diagnosis in tumor patients.

An anti-human lung cancer monoclonal antibody LC128, which shows a strong positive reaction with human lung cancer tissues and lung cancer cell lines, A549, Calu-3, NCI-H1975, NCI-H460, SK-LU-1, NCI-H157, while is not cross-reactive with normal human lung tissues and other non-lung cancer cells can be screened and produced. The antigen epitope recognized by the antibody LC128 is Neu5Acα2-6GlcNAcβ1-3Galβ1-3GlcNAcβ1-3Galβ1, a lung cancer marker. An immunomagnetic bead method for detecting human lung cancer based on the high sensitivity of the antibody LC128 has been developed.

DETAILED DESCRIPTION OF PREFERRED EMBODIMENT(S)

A lung cancer tumor marker—an abnormally glycosylated β1 subunit of integrin, named N3G4 is disclosed. A hybridoma cell strain producing an anti-N3G4 monoclonal antibody LC128 which can recognize Neu5Acα2-6GlcNAcβ1-3Galβ1-3GlcNAcβ1-3Galβ1 as antigen epitope is also disclosed. This monoclonal antibody shows a strong positive reaction with human lung cancer tissues and lung cancer cell lines, A549, Calu-3, NCI-H1975, NCI-H460, SK-LU-1, NCI-H157, and is not cross-reactive with normal human lung tissues and other non-lung cancer cells. A method for in vitro diagnosis of lung cancer by using immunomagnetic beads (LC128-MB) based on the monoclonal antibody LC128 is also disclosed.

More specifically, an abnormally glycosylated human lung cancer tumor marker N3G4 is provided, which is an abnormally glycosylated β1 subunit of integrin having a saccharide structure of Neu5Acα2-6GlcNAcβ1-3Galβ1-3GlcNAcβ1-3Galβ1 as antigen epitope at the β1 subunit.

In some preferred embodiments, the amino acid sequence of the β1 subunit of integrin is as shown by SEQ ID No: 1 (β1).

An antibody can be directed against the disclosed human lung cancer marker N3G4, which is capable of specifically recognizing the saccharide structure Neu5Aca2-6Glc-NAcb1-3Galb1-3GlcNAcb1-3Galb1 as antigen epitope, wherein the antibody can be a polyclonal antibody or a monoclonal antibody, preferably a monoclonal antibody.

A kit for detecting human lung cancer comprising the disclosed antibody LC128 can be made. In some preferred embodiments, the antibody is anti-N3G4 monoclonal antibody LC128 secreted by the hybridoma cell strain with an accession number of CGMCC No. 10414.

A conjugate can comprise the human lung cancer marker N3G4 and a substance selected from the group consisting of biolabels, anti-tumor drugs, toxins, and radioactive agents.

A kit for the detection or treatment of human lung cancer can comprise the disclosed antibodies.

In some preferred embodiments of the kit, the detection is performed by coupling the monoclonal antibody LC128 with magnetic nanoparticles, preferably by coupling the antibody LC128 with magnetic nanoparticles to form anti-lung cancer immunomagnetic beads (LC128-MB). In some preferred embodiments, the sample to be tested is human hydrothorax or sputum containing exfoliated human lung cancer cells.

A hybridoma cell strain can secrete the anti-N3G4 monoclonal antibody LC128. The hybridoma cell strain has been deposited at CGMCC (China General Microbiological Culture Collection Center, address: Institute of Microbiology Chinese Academy of Science, 3#, No. 1 West Beichen Road, Chaoyang District, Beijing, China) on Mar. 25, 2015, with an accession number of CGMCC No. 10414 and a taxonomic designation of anti-human lung cancer monoclonal antibody LC128 hybridoma cell strain.

EXAMPLES

The examples are provided for illustration and are not meant to be limiting. Experimental conditions and procedures which are not specifically indicated should be generally carried out according to conventional processes such as those described in Sambrook et al., Molecular Cloning: A Laboratory Manual (New York: Cold Spring Harbor Laboratory Press, 1989), or according to the manufacturer's instructions. Unless otherwise indicated, percentages and parts are based on weight.

Methods or materials similar or equivalent to those disclosed herein can be applied. The preferred embodiments and materials are provided herein only for illustration.

Example 1

Production and Purification of Monoclonal Antibody LC128

(1) Preparation of Hybridoma

1) Immunization of animals and culturing of cells: Balb/C mice (purchased from Beijing Vital River Laboratory Animal Technology Co., Ltd.) were immunized with fresh protein homogenate of human lung cancer tissue, at a dose of 10 μg total protein/mouse by intraperitoneal injection (i.p.). After 2 weeks, the mice were immunized again by injecting human lung cancer tissue homogenate in the same manner (same volume and process) as described above. After obtaining a desired serum titer in the mice tested, the mice were boosted. At Day 3 after the boosting, the spleens of the mice were harvest and prepared into a suspension of lymphocytes for cell fusion. Myeloma cells Sp2/0 (ATCC CRL-1772) were recovered 2 weeks before cell fusion. To ensure the sensitivity of the cells to HAT, the cells were screen once by using 8-AG (8-azaguanine) to prevent, or at least reduce, the cells form mutating.

2) Cell fusion: Cell fusion was carried out using the suspension of lymphocytes and the myeloma cells prepared in step 1), according to the procedure as described in "Short Protocols in Immunology", John E, Coligan, et al., Science Press, September 2009). The resulting suspension of fused cells were cultured in a culture medium containing feeder cells (macrophages from mouse peritoneal cavity as feeder cells). After 24-hour fusion, HAT selection medium (purchased from Invitrogen; HAT, i.e., H: Hypoxanthine, A: Aminopterin, and T: Thymidine) for selective culturing.

3) Antibody Detection: Hybridoma cell strains were detected by ELISA for the secretion of antibodies. The procedure was as follows: A549 cells ($1 \times 10^4$ cells/well, 96-well plate) were incubated in an incubator at 37° C., 5% $CO_2$ for 24 h. After adherence, the cells were first washed once with PBS (phosphate-buffered saline), and then immobilized with 4% paraformaldehyde at room temperature for 10 min before washing with PBS for 3 times. Then, 100 μl of the supernatant to be tested was added and incubated at 37° C. for 1 h. After washing for 3 times, HRP-labeled anti-mouse second antibodies, IgG-HRP (purchased from ZSGB-BIO), were added and incubated at 37° C. for 1 h. After washing for 3 times, 50 μl of TMB (purchased from ZSGB-BIO) was added and allowed to stand at room temperature for chromogenic reaction. After 5-min reaction, 50 μl of stop buffer was added. Optical Density (OD) values at 450 nm were measured by using a plate reader. An OD value which is 2-fold or more larger than that of negative control was considered as a positive result.

4) Amplification and cryopreservation of hybridoma: Hybridoma cells screened as positive were amplified by limiting dilution using mouse peritoneal cavity macrophages as feeder cells. After 2-3 rounds of amplification, hybridoma cells capable of stably producing monoclonal antibodies of a high titer were amplified and cryopreserved.

A positive hybridoma cell strain, which can produce anti-human lung cancer monoclonal antibodies, was obtained. The hybridoma cell strain was deposited at CGMCC (China General Microbiological Culture Collection Center, address: Institute of Microbiology Chinese Academy of Science, No. 1 West Beichen Road, Chaoyang District, Beijing, China) on Mar. 25, 2015, with an accession number of CGMCC No. 10414.

(2) Production and Purification of Monoclonal Antibody LC128

The hybridoma cell strain (CGMCC No. 10414) which can stably secrete the monoclonal antibody LC128 was amplified. Cell culture supernatant was then collected. The monoclonal antibody LC128 was purified by Protein G affinity chromatography. Cell culture supernatant containing the monoclonal antibody LC128 was loaded onto a Protein G affinity chromatography column (purchased from GE) pre-equilibrated with PBS. The column was then washed with PBS until the OD of the eluate close to zero, and eluted with 0.2 M Glycine-HCL solution (pH 2.8). Fractions were collected and measured for their OD values. The Fractions containing the peak were kept, dialyzed, and concentrated before storage at −20° C.

Example 2

Identification of LC128 Monoclonal Antibody

Figure 1:
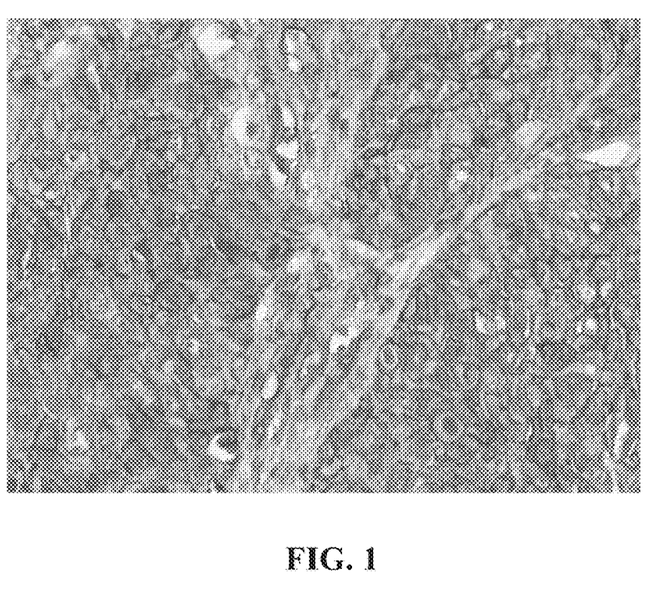
FIG. 1 shows the result of immunohistochemistry staining of a human lung cancer tissue section by using monoclonal antibody LC128.
Figure 2:
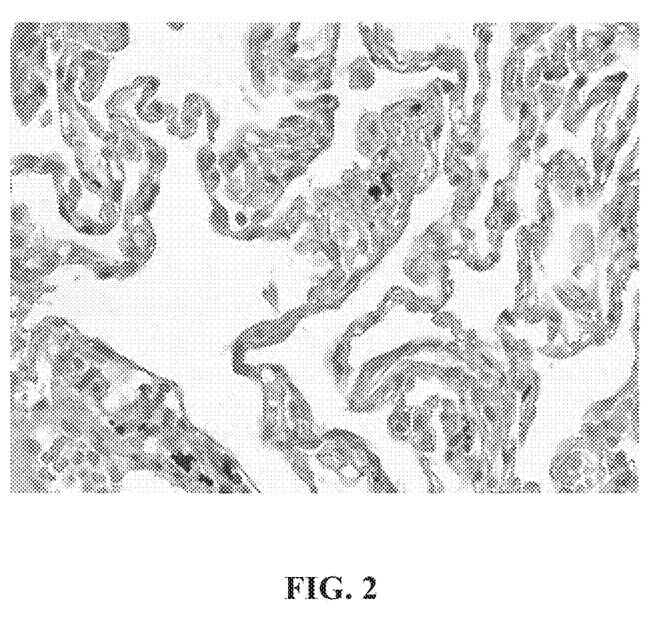
FIG. 2 shows the result of immunohistochemistry staining of a normal human lung tissue section by using monoclonal antibody LC128.

Sections of human lung cancer tissues and of normal human lung tissues were stained using the monoclonal antibody LC128 produced in Example 1. The results (FIG. 1 and FIG. 2) show a positive reaction for the immunohistochemistry staining of the sections of human lung cancer tissues by using the monoclonal antibody LC128 (FIG. 1), while a negative reaction for that of normal human lung tissues (FIG. 2).

Figure 3:
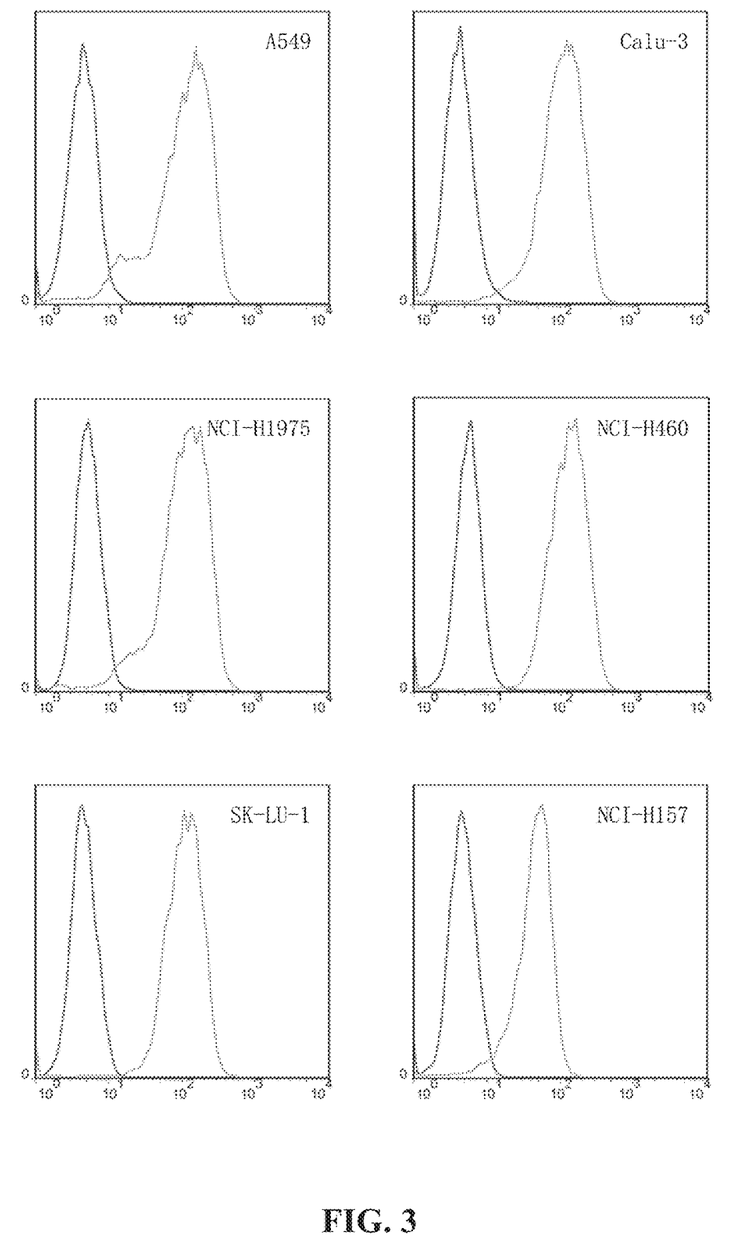
FIG. 3 shows the results of flow cytometry of lung cancer cell lines A549, Calu-3, NCI-H1975, NCI-H460, SK-LU-1, NCI-H157 by using monoclonal antibody LC128.

Flow cytometry was performed by using the monoclonal antibody LC128 produced in Example 1 and human lung cancer cell lines Calu-3, NCI-H1975, NCI-H460, SK-LU-1, NCI-H157 and other non-lung cancer cell lines. Immunohistochemistry tests of human lung cancer tissues, normal human lung tissues and other human tissues were carried out by using the antibody. The results (Table 1, Table 2 and FIG. 3) show a strong positive reaction between the antibody LC128 and human lung cancer tissues and lung cancer cell lines A549, Calu-3, NCI-H1975, NCI-H460, SK-LU-1, NCI-H157, while no cross-reaction between the antibodies and normal human lung tissues and other non-lung cancer cells.

TABLE 1

Detection of Immunoreaction of Anti-Lung Cancer Monoclonal Antibody LC128 with Various Cells by Flow Cytometry

| Cell Lines | Antibody LC128 |
| --- | --- |
| human pulmonary adenocarcinoma cell line A549 | + |
| human pulmonary adenocarcinoma cell line Calu-3 | + |
| human non-small cell pulmonary adenocarcinoma cell line NCI-H1975 | + |
| human large cell lung cancer cell line NCI-H460 | + |
| human poorly differentiated pulmonary adenocarcinoma cell line SK-LU-1 | + |
| human non-small cell pulmonary adenocarcinoma cell line NCI-H157 | + |
| human colon cancer cell line LoVo | − |
| human colon cancer cell line SW480 | − |
| human colon cancer cell line HT29 | − |
| human stomach cancer cell line MKN45 | − |
| human stomach cancer cell line MGC-803 | − |
| human hepatocellular carcinoma cell line HepG2 | − |
| human hepatocellular carcinoma cell line Huh7 | − |
| human hepatocellular carcinoma cell line Hep3B | − |
| human cervical cancer cell line HeLa | − |
| human embryonic kidney cell line 293 | − |
| human brain glioma cell line U373 | − |
| human kidney cancer cell line 769-P | − |
| human kidney cancer cell line ACHN | − |
| human breast cancer cell line MCF7 | − |
| human prostate cancer cell line PC1 | − |
| human prostate cancer cell line LNCaP | − |
| human prostate cancer cell line DU145 | − |
| human chronic leukemia cell line K562 | − |
| normal human peripheral blood monocyte PBMC | − |

TABLE 2

Immunohistochemistry Detection of the Immunoreaction Of Anti-Human Lung Cancer Monoclonal Antibody LC128 with Various Tissues

| Tissue (cancer tissues and normal tissues) | Antibody LC128 |
| --- | --- |
| human pulmonary adenocarcinoma tissue (patient #1) | +++ |
| normal human lung tissue (patient #1) | − |
| human pulmonary adenocarcinoma tissue (patient #2) | +++ |
| normal human lung tissue (patient #2) | − |
| human pulmonary adenocarcinoma tissue (patient #3) | ++ |
| normal human lung tissue (patient #3) | − |
| human pulmonary adenocarcinoma tissue (patient #4) | ++ |
| normal human lung tissue (patient #4) | − |
| human pulmonary adenocarcinoma tissue (patient #1) | +++ |
| normal human lung tissue (patient #1) | − |
| human kidney cancer tissue | − |
| normal human kidney tissue | − |
| human stomach cancer tissue | − |
| normal human stomach tissue | − |
| human liver cancer tissue | − |
| normal human liver tissue | − |
| human breast cancer tissue | − |
| normal human breast tissue | − |
| human prostate cancer tissue | − |
| normal human prostate tissue | − |
| human kidney cancer tissue | − |
| normal human kidney tissue | − |
| human esophageal cancer tissue | − |
| normal human esophageal tissue | − |
| human colon cancer tissue | − |
| normal human colon tissue | − |

Example 3

Production of N3G4 Antigen

1) Cell collection: Human lung cancer cell line A594 cells were cultured in RPMI-1640 medium (purchased from Invitrogen) containing 10% FBS. $1\times10^8$ A594 cells were collected.

2) Immunoprecipitation: After washing with PBS for 3 times, 100 μg of the monoclonal antibody LC128 were added and incubated at 4° C. for 2 h before washing additionally with PBS for 3 times. 1 ml of lysis buffer (50 mM Tris-HCl, pH 8.0; 150 mM NaCl; 0.02% sodium azide; 0.1% SDS; 100 μg/ml PMSF (Phenylmethanesulfonyl fluoride); 1 μg/ml Aprotinin; 1% NP-40; 0.5% sodium deoxycholate) was add for lysis on ice-bath for 30 min. Centrifugation at 12,000 g was performed for 10 min to provide a supernatant.

Figure 4:
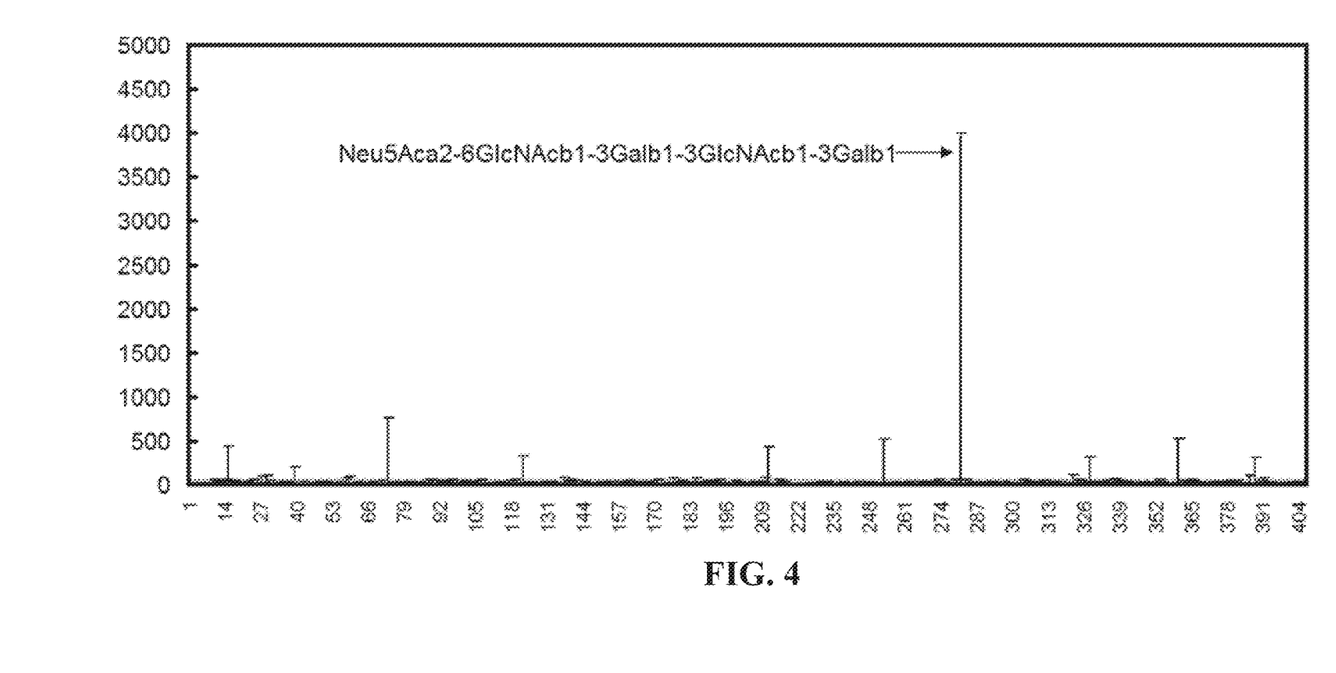
FIG. 4 shows the result of carbohydrate chip test.
Figure 5:
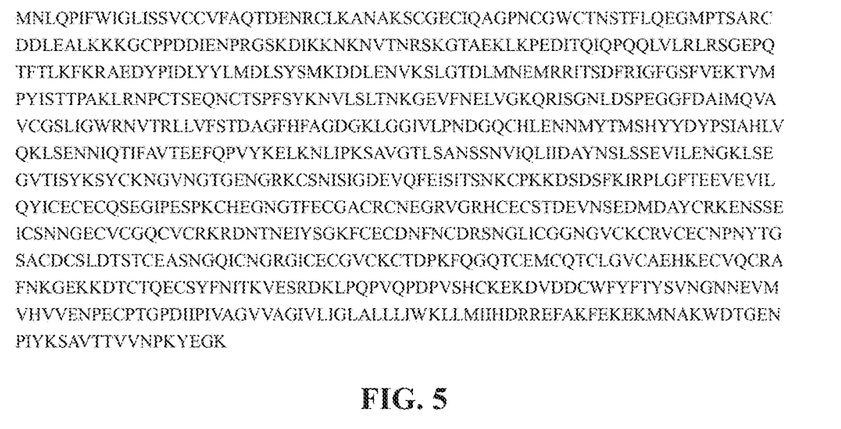
FIG. 5 is the amino acid sequence of the β1 subunit of integrin.

3) Identification of antigen: The supernatant collected in step 2) was loaded onto a Protein G affinity chromatography column. The column was then washed with PBS until the OD value of eluate was close to 0, and then eluted with 0.2 M Glycine-HCL solution (pH 2.8). Fractions were collected and measured for their OD values. The Fractions containing the peak were kept and analyzed by now abandoned mass spectrum. The results of mass spectrum (Table 3) showed that the antigen of LC128 is integrin ITGB1. The results of carbohydrate chip test of LC128 (FIG. 4) showed that the antigen epitope recognized by the monoclonal antibody LC128 is the saccharide structure Neu5Acα2-3Galβ1-3GlcNAcβ1-3Galβ1-3GlcNAcβ, which is a sugar chain on the β1 subunit of human integrin α3β1 dimer. The monoclonal antibody LC128 only specifically recognized human lung cancer cells and human lung cancer tissues, indicating that the antigen is an abnormally glycosylated β1 subunit of integrin, and has an epitope Neu5Acα2-6GlcNAcβ1-3Galβ1-3GlcNAcβ1-3Galβ1 which expressed only on human lung cancer tissue cells.

TABLE 3

Identification of the antigen of LC128 by mass spectrum

| Accession | Mass | Score |
|---|---|---|
| ITGB1 HUMAN | 183572 | 176 |
| Keratin 17 HUMAN | 56937 | 45 |
| Albumin HUMAN | 21465 | 37 |
| Actin, gamma 1 HUMAN | 63258 | 35 |
| Desmoglein 1 HUMAN | 15763 | 35 |
| Histone H2B HUMAN | 18579 | 30 |
| Keratin 6B HUMAN | 35336 | 30 |
| Keratin 1B HUMAN | 74350 | 28 |
| Keratin 15 HUMAN | 26537 | 25 |
| Keratin 83 HUMAN | 15483 | 20 |

Example 4

Preparation of Immunological Diagnostic Agent for Human Lung Cancer

The monoclonal antibody LC128 was coupled with magnetic nanoparticles to form anti-lung cancer immunomagnetic beads (LC128-MB). The beads were mixed with hydrothorax for the capture and enrichment of exfoliated lung cancer cells. Then, diagnosis can be performed under a microscope after Wright-Giemsa pathological staining. The kit is useful for early screening, prognosis monitoring, and pathologically assistant diagnosis in tumor patients. It has been demonstrated by experiments that the human lung cancer diagnostic agent as disclosed is advantageous. The agent has a higher sensitivity than conventional detection methods of exfoliated cells, due to enrichment effect of the immunomagnetic beads coupled with the monoclonal antibody LC128. The agent has high specificity due to the use of the magnetic beads coupled with the antibody LC128 which can specifically recognize and bind to lung cancer tissue cells (and not non-lung cancer cells). The agent is also convenient and economical to use due to the high sensitivity and specificity of the method, and high detection rate.

Specific procedure was as follows:

1) Hydrothorax collection: Lung cancer patients were from Shanghai East Hospital, The First Hospital of Jilin University, and The Second Affiliated Hospital of Kunming Medical University.

2) Lung cancer cells enrichment: The magnetic particles coupled with the antibody LC128 were incubated with the hydrothorax from the patients at room temperature for 20 min. The magnetic particles were then separated from the hydrothorax by using a magnetic separator to enrich lung cancer cells.

3) Wright-Giemsa pathological staining: The lung cancer cells enriched in step 2) were stained by Wright-Giemsa pathological staining, and prepared onto slides for detection under microscope.

4) Detection under microscope: The results of the pathological staining were analyzed according to the morphological features of lung cancer cells.

The result comparison of detection rates between the LC128-MB method and conventional smear methods for hydrothorax of 137 lung cancer patients from the three hospitals (Tables 4, 5, and 6) showed that, the positive detection rate was 86.13% (118/137) for the LC128-MB method, while it was only 40.88% (56/137) for conventional exfoliated cells smear method. Therefore, N3G4 specifically expressed by lung cancer cells is a promising lung cancer marker, and the disclosed anti-lung cancer immunomagnetic bead (LC128-MB) is a simple and efficient diagnostic agent for lung cancer.

TABLE 4

| Patient No. (Shanghai) | Conventional smear method | LC128-MB Method |
|---|---|---|
| #1 | + | + |
| #2 | − | + |
| #3 | − | + |
| #4 | + | − |
| #5 | − | + |
| #6 | + | + |
| #7 | − | + |
| #8 | − | + |
| #9 | − | + |
| #10 | + | + |
| #11 | − | + |
| #12 | + | − |
| #13 | − | + |
| #14 | + | + |
| #15 | − | + |
| Total | 40.00% (6/15) | 80.00% (12/15) |

TABLE 5

| Patient No. (Changchun) | Conventional smear method | LC128-MB Method |
|---|---|---|
| #1 | + | + |
| #2 | − | + |
| #3 | − | + |
| #4 | + | + |
| #5 | − | − |
| #6 | + | + |
| #7 | − | + |

TABLE 5-continued

| Patient No. (Changchun) | Conventional smear method | LC128-MB Method |
|---|---|---|
| #8 | + | + |
| #9 | − | + |
| #10 | + | + |
| #11 | − | + |
| #12 | − | + |
| #13 | − | + |
| #14 | + | + |
| #15 | + | + |
| #16 | − | − |
| #17 | + | + |
| #18 | − | + |
| #19 | − | + |
| #20 | + | − |
| #21 | − | + |
| #22 | − | + |
| #23 | + | + |
| #24 | − | + |
| #25 | + | − |
| #26 | − | + |
| #27 | − | + |
| #28 | + | + |
| #29 | + | + |
| #30 | − | − |
| #31 | + | + |
| #32 | + | + |
| #33 | − | + |
| #34 | − | + |
| #35 | + | − |
| #36 | − | + |
| #37 | − | + |
| #38 | + | + |
| #39 | − | + |
| #40 | − | + |
| #41 | + | + |
| #42 | − | + |
| #43 | − | + |
| #44 | + | + |
| #45 | − | + |
| #46 | − | − |
| #47 | + | + |
| #48 | − | + |
| #49 | + | + |
| #50 | + | + |
| #51 | − | + |
| #52 | − | + |
| #53 | + | + |
| #54 | − | + |
| #55 | − | + |
| #56 | − | + |
| Total | 41.07% (23/56) | 87.50% (49/56) |

TABLE 6

| Patient No. (Kunming) | Conventional smear method | LC128-MB Method |
|---|---|---|
| #1 | + | + |
| #2 | − | + |
| #3 | − | + |
| #4 | − | + |
| #5 | + | + |
| #6 | + | + |
| #7 | − | + |
| #8 | + | + |
| #9 | − | − |
| #10 | − | + |
| #11 | − | − |
| #12 | + | + |
| #13 | + | + |
| #14 | − | + |
| #15 | − | + |
| #16 | + | − |
| #17 | − | + |
| #18 | − | + |
| #19 | − | + |
| #20 | − | + |
| #21 | + | + |
| #22 | − | + |
| #23 | − | − |
| #24 | + | + |
| #25 | + | + |
| #26 | − | + |
| #27 | + | + |
| #28 | − | + |
| #29 | + | − |
| #30 | − | + |
| #31 | − | + |
| #32 | + | + |
| #33 | + | + |
| #34 | − | + |
| #35 | − | + |
| #36 | + | − |
| #37 | + | + |
| #38 | + | + |
| #39 | − | + |
| #40 | − | + |
| #41 | + | + |
| #42 | + | + |
| #43 | − | + |
| #44 | − | + |
| #45 | − | + |
| #46 | + | + |
| #47 | − | − |
| #48 | + | + |
| #49 | − | + |
| #50 | − | + |
| #51 | + | + |
| #52 | − | + |
| #53 | + | + |
| #54 | − | − |
| #55 | − | + |
| #56 | + | + |
| #57 | − | + |
| #58 | − | + |
| #59 | − | + |
| #60 | + | + |
| #61 | + | + |
| #62 | − | − |
| #63 | − | + |
| #64 | + | + |
| #65 | − | + |
| #66 | − | + |
| Total | 40.91% (27/66) | 86.36% (57/66) |

The viable biological material (strain) was received by the China General Microbiological Culture Collection Center (CGMCC) which acted as the depositary on Mar. 25, 2015. The CGMCC is located at No. 1 Beichen West Road, Chaoyang District, Beijing, INSTITUTE OF MICROBIOLOGY, 100101.

The strain was identified as LC128 and designated as a hybridoma cell strain secreting an anti-human lung cancer monoclonal antibody LC128. The strain was given the accession number 10414. The strain shall be available for at least 30 years.

While particular elements, embodiments and applications of the present invention have been shown and described, it will be understood, that the invention is not limited thereto since modifications can be made without departing from the scope of the present disclosure, particularly in the light of the foregoing teachings.

What is claimed is:

1. An antibody against a human lung cancer tumor marker N3G4, wherein said marker is an abnormally glycosylated β1 subunit of integrin, wherein said abnormally glycosylated β1 subunit of integrin is a β1 subunit of integrin having a saccharide structure of Neu5Acα2-6GlcNAcβ1-3Galβ1-3GlcNAcβ1-3Galβ1 as an antigen epitope, wherein said antibody is capable of specifically recognizing said saccharide structure of Neu5Acα2-6GlcNAcβ1-3Galβ1-3GlcNAcβ1-3Galβ1 as said antigen epitope, wherein said antibody is a monoclonal antibody LC128.

2. A method for manufacturing an agent for the diagnosis or treatment of human lung cancer using said monoclonal antibody LC128 of claim 1, said method comprising:
   (a) coupling said monoclonal antibody LC128 with a plurality of magnetic nanoparticles to form a plurality of immunomagnetic beads; and
   (b) conjugating said monoclonal antibody LC128 to a component, wherein said component is a biolabel, an anti-tumor drug, a toxin, a radioactive agent or a magnetic bead.

3. A conjugate comprising:
   a) said antibody of claim 1; and
   b) a component, wherein said component is a biolabel, an anti-tumor drug, a toxin, a radioactive agent or a magnetic bead.

4. A pharmaceutical composition comprising:
   a) said antibody of claim 1; and
   b) a pharmaceutically accepted carrier, diluent or excipient.

5. A hybridoma cell strain secreting an antibody LC128, wherein said antibody LC128 targets a human lung cancer β1 subunit of integrin, and wherein said hybridoma cell strain has an accession number of CGMCC No. 10414.

6. The antibody of claim 1, wherein said monoclonal antibody LC128 is secreted by a hybridoma cell strain with an accession number of CGMCC No. 10414.

7. A pharmaceutical composition comprising:
   a) said conjugate of claim 3; and
   b) a pharmaceutically accepted carrier, diluent or excipient.

8. A kit for the diagnosis or treatment of human lung cancer, comprising said monoclonal antibody LC128 of claim 1.

9. A kit for the diagnosis or treatment of human lung cancer comprising said conjugate of claim 3.

10. The antibody of claim 1, wherein the amino acid sequence of said β1 subunit of integrin is as shown by SEQ ID No:1.

11. A method for diagnosis or treatment of human lung cancer comprising:
   (a) using an antibody against a human lung cancer tumor marker N3G4, wherein said marker is an abnormally glycosylated β1 subunit of integrin is a β1 subunit of integrin having a saccharide structure of Neu5Acα2-6GlcNAcβ1-3Galβ1-3GlcNAcβ1-3Galβ1 as an antigen epitope, wherein said antibody is capable of recognizing said saccharide structure of Neu5Acα2-6GlcNAcβ1-3Galβ1-3GlcNAcβ1-3Galβ1 as said antigen epitope, and wherein said antibody is a monoclonal antibody LC128;
   (b) performing an immunomagnetic bead assay, wherein said assay comprises coupling said monoclonal antibody LC128 with a plurality of magnetic nanoparticles to form a plurality of immunomagnetic beads; and
   (c) detecting said saccharide structure of Neu5Acα2-6GlcNAcβ1-3Galβ1-3GlcNAcβ1-3Galβ1 in a sample using said plurality of immunomagnetic beads.

12. The method of claim 11, further comprising:
   (d) conjugating said monoclonal antibody LC128 to a component, wherein said component is a biolabel, an anti-tumor drug, a toxin, a radioactive agent or a magnetic bead.

13. The method of claim 11, wherein said sample is a human hydrothorax containing a plurality of exfoliated human lung cancer cells.

14. The method of claim 11, further comprising:
   (d) suspending said monoclonal antibody LC128 in a pharmaceutically accepted carrier, diluent or excipient.

* * * * *

SEQUENCE LISTING

<160> NUMBER OF SEQ ID NOS: 1

<210> SEQ ID NO 1
<211> LENGTH: 798
<212> TYPE: PRT
<213> ORGANISM: Homo sapiens

<400> SEQUENCE: 1

Met Asn Leu Gln Pro Ile Phe Trp Ile Gly Leu Ile Ser Ser Val Cys
1               5                   10                  15

Cys Val Phe Ala Gln Thr Asp Glu Asn Arg Cys Leu Lys Ala Asn Ala
            20                  25                  30

Lys Ser Cys Gly Glu Cys Ile Gln Ala Gly Pro Asn Cys Gly Trp Cys
        35                  40                  45

Thr Asn Ser Thr Phe Leu Gln Glu Gly Met Pro Thr Ser Ala Arg Cys
    50                  55                  60

Asp Asp Leu Glu Ala Leu Lys Lys Lys Gly Cys Pro Pro Asp Asp Ile
65                  70                  75                  80

Glu Asn Pro Arg Gly Ser Lys Asp Ile Lys Lys Asn Lys Asn Val Thr
                85                  90                  95

Asn Arg Ser Lys Gly Thr Ala Glu Lys Leu Lys Pro Glu Asp Ile Thr
            100                 105                 110

Gln Ile Gln Pro Gln Gln Leu Val Leu Arg Leu Arg Ser Gly Glu Pro
        115                 120                 125

Gln Thr Phe Thr Leu Lys Phe Lys Arg Ala Glu Asp Tyr Pro Ile Asp
    130                 135                 140

Leu Tyr Tyr Leu Met Asp Leu Ser Tyr Ser Met Lys Asp Asp Leu Glu
145                 150                 155                 160

Asn Val Lys Ser Leu Gly Thr Asp Leu Met Asn Glu Met Arg Arg Ile
                165                 170                 175

Thr Ser Asp Phe Arg Ile Gly Phe Gly Ser Phe Val Glu Lys Thr Val
            180                 185                 190

Met Pro Tyr Ile Ser Thr Thr Pro Ala Lys Leu Arg Asn Pro Cys Thr
        195                 200                 205

Ser Glu Gln Asn Cys Thr Ser Pro Phe Ser Tyr Lys Asn Val Leu Ser
    210                 215                 220

Leu Thr Asn Lys Gly Glu Val Phe Asn Glu Leu Val Gly Lys Gln Arg
225                 230                 235                 240

Ile Ser Gly Asn Leu Asp Ser Pro Glu Gly Gly Phe Asp Ala Ile Met
                245                 250                 255

Gln Val Ala Val Cys Gly Ser Leu Ile Gly Trp Arg Asn Val Thr Arg
            260                 265                 270

Leu Leu Val Phe Ser Thr Asp Ala Gly Phe His Phe Ala Gly Asp Gly
        275                 280                 285

Lys Leu Gly Gly Ile Val Leu Pro Asn Asp Gly Gln Cys His Leu Glu
    290                 295                 300

Asn Asn Met Tyr Thr Met Ser His Tyr Tyr Asp Tyr Pro Ser Ile Ala
305                 310                 315                 320

His Leu Val Gln Lys Leu Ser Glu Asn Asn Ile Gln Thr Ile Phe Ala
                325                 330                 335

Val Thr Glu Glu Phe Gln Pro Val Tyr Lys Glu Leu Lys Asn Leu Ile
            340                 345                 350

Pro Lys Ser Ala Val Gly Thr Leu Ser Ala Asn Ser Ser Asn Val Ile
        355                 360                 365

```
Gln Leu Ile Ile Asp Ala Tyr Asn Ser Leu Ser Ser Glu Val Ile Leu
370                 375                 380

Glu Asn Gly Lys Leu Ser Glu Gly Val Thr Ile Ser Tyr Lys Ser Tyr
385                 390                 395                 400

Cys Lys Asn Gly Val Asn Gly Thr Gly Glu Asn Gly Arg Lys Cys Ser
                405                 410                 415

Asn Ile Ser Ile Gly Asp Glu Val Gln Phe Glu Ile Ser Ile Thr Ser
                420                 425                 430

Asn Lys Cys Pro Lys Lys Asp Ser Asp Ser Phe Lys Ile Arg Pro Leu
            435                 440                 445

Gly Phe Thr Glu Glu Val Glu Val Ile Leu Gln Tyr Ile Cys Glu Cys
450                 455                 460

Glu Cys Gln Ser Glu Gly Ile Pro Glu Ser Pro Lys Cys His Glu Gly
465                 470                 475                 480

Asn Gly Thr Phe Glu Cys Gly Ala Cys Arg Cys Asn Glu Gly Arg Val
                485                 490                 495

Gly Arg His Cys Glu Cys Ser Thr Asp Glu Val Asn Ser Glu Asp Met
                500                 505                 510

Asp Ala Tyr Cys Arg Lys Glu Asn Ser Ser Glu Ile Cys Ser Asn Asn
            515                 520                 525

Gly Glu Cys Val Cys Gly Gln Cys Val Cys Arg Lys Arg Asp Asn Thr
530                 535                 540

Asn Glu Ile Tyr Ser Gly Lys Phe Cys Glu Cys Asp Asn Phe Asn Cys
545                 550                 555                 560

Asp Arg Ser Asn Gly Leu Ile Cys Gly Gly Asn Gly Val Cys Lys Cys
                565                 570                 575

Arg Val Cys Glu Cys Asn Pro Asn Tyr Thr Gly Ser Ala Cys Asp Cys
                580                 585                 590

Ser Leu Asp Thr Ser Thr Cys Glu Ala Ser Asn Gly Gln Ile Cys Asn
            595                 600                 605

Gly Arg Gly Ile Cys Glu Cys Gly Val Cys Lys Cys Thr Asp Pro Lys
610                 615                 620

Phe Gln Gly Gln Thr Cys Glu Met Cys Gln Thr Cys Leu Gly Val Cys
625                 630                 635                 640

Ala Glu His Lys Glu Cys Val Gln Cys Arg Ala Phe Asn Lys Gly Glu
                645                 650                 655

Lys Lys Asp Thr Cys Thr Gln Glu Cys Ser Tyr Phe Asn Ile Thr Lys
                660                 665                 670

Val Glu Ser Arg Asp Lys Leu Pro Gln Pro Val Gln Pro Asp Pro Val
            675                 680                 685

Ser His Cys Lys Glu Lys Asp Val Asp Asp Cys Trp Phe Tyr Phe Thr
            690                 695                 700

Tyr Ser Val Asn Gly Asn Asn Glu Val Met Val His Val Val Glu Asn
705                 710                 715                 720

Pro Glu Cys Pro Thr Gly Pro Asp Ile Ile Pro Ile Val Ala Gly Val
                725                 730                 735

Val Ala Gly Ile Val Leu Ile Gly Leu Ala Leu Leu Leu Ile Trp Lys
                740                 745                 750

Leu Leu Met Ile Ile His Asp Arg Arg Glu Phe Ala Lys Phe Glu Lys
            755                 760                 765

Glu Lys Met Asn Ala Lys Trp Asp Thr Gly Glu Asn Pro Ile Tyr Lys
770                 775                 780
```

```
Ser Ala Val Thr Thr Val Val Asn Pro Lys Tyr Glu Gly Lys
785                 790                 795
```